United States Patent [19]

Bresak et al.

[11] Patent Number: 4,542,014

[45] Date of Patent: Sep. 17, 1985

[54] HAIR TREATING COMPOSITION

[75] Inventors: Ann F. Bresak; Eva Tolgyesi, both of Rockville, Md.

[73] Assignee: The Gillette Company, Boston, Mass.

[21] Appl. No.: 446,733

[22] Filed: Dec. 3, 1982

[51] Int. Cl.$^4$ .................... A61K 7/06; A61K 7/08; A61K 7/11; A61K 47/00

[52] U.S. Cl. .................... 424/70; 132/7; 514/773; 514/777

[58] Field of Search .................... 536/20; 424/70, 359, 424/361

[56] References Cited

U.S. PATENT DOCUMENTS

| | | | |
|---|---|---|---|
| 3,879,376 | 4/1975 | Vanlerberghe et al. | 536/20 |
| 3,953,608 | 4/1976 | Vanlerberghe et al. | 536/20 |
| 4,031,025 | 6/1977 | Vanlerberghe et al. | 424/361 |
| 4,134,412 | 1/1979 | Gross et al. | 536/20 |
| 4,186,188 | 1/1980 | Gumprecht | 424/359 X |
| 4,390,525 | 6/1983 | Yoshioka et al. | 424/359 X |

FOREIGN PATENT DOCUMENTS

| | | | |
|---|---|---|---|
| 865694 | 3/1971 | Canada | 424/359 |
| 2222733 | 11/1972 | Fed. Rep. of Germany | 536/20 |
| 2354760 | 1/1978 | France | 424/361 |

OTHER PUBLICATIONS

Horowitz et al., Journal of American Chemical Society, 1957, vol. 79, pp. 5046 to 5049.

*Primary Examiner*—Dale R. Ore
*Attorney, Agent, or Firm*—Mandel E. Slater

[57] ABSTRACT

This invention deals with aqueous hair treating compositions utilizing adducts of (1) low molecular weight aminopolysaccharides derived from chitosan with (2) hydrolyzed keratin protein comprising mixtures of amino acids.

4 Claims, No Drawings

HAIR TREATING COMPOSITION

BACKGROUND

This invention deals with aqueous hair treating compositions utilizing adducts of (1) low molecular weight aminopolysaccharides derived from chitosan with (2) hydrolyzed keratin protein comprising mixtures of amino acids.

Many hair care products contain polymeric ingredients for the purpose of improving attributes such as set holding and the property perceived as "body". Unfortunately, these polymers may undesirably alter other attributes such as feel, sheen, or hair combing ease. This is due in part to the fact that many polymers produce fiber coatings which have surface friction and reflectance properties very different from clean, intact hair.

It is also known to use a wide variety of protein materials in the formulation of modern hair care products to provide good feel and combing properties. However, such materials have been found to be generally ineffective in increasing set holding to any great extent.

We have discovered a class of materials, which when formulated in conventional aqueous hair treating compositions such as shampoos and conditioning rinses, provides an unexpected combination of set holding and conditioning benefits. In addition, a smooth, soft feel is imparted to the hair and combing, both wet and dry, is markedly improved. Furthermore, the hair appears to have more body, exhibits improved luster, and, unexpectedly, provides improved set holding than is the case when either of the individual ingredients is employed alone.

These benefits are derived from the inclusion of certain adducts of (1) low molecular weight aminopolysaccharides derived from chitosan with (2) hydrolyzed keratin protein comprising mixtures of amino acids as will be hereinafter more fully described.

The exact nature of the mode of action of these adducts in enhancing set improvement and combing properties of treated hair is not known. It is known, however, that aminopolysaccharides are used in the food industry to precipitate proteinaceous materials from beverage compositions by forming adducts. It is thus theorized that our mixtures of low molecular weight aminopolysaccharides derived from chitosan and hydrolyzed keratin protein may penetrate hair fibers, forming adducts with each other and with the keratin protein. This network may then act on cuticle layers to form a more uniform surface manifested in enhanced combing and to provide some rigidity to the cortex manifested as enhanced set holding.

To determine the depth of penetration into hair fibers and to possibly substantiate formation of adducts in the fiber, known staining techniques were employed to show significant staining of the cuticular area of treated fibers along with staining of a portion of the cortical area inside the cuticle. It is our opinion that this evidence, along with the lack of significant surface coating as determined by scanning electronmicroscopy, points strongly to interior adduct formation.

The prior art contains many references to the use of a wide variety of protein materials in hair treating compositions. Among these may be mentioned Canadian Pat. No. 865,694, describing cosmetic compositions for the treatment of hair which contain polypeptides obtained by heating collagen-containing materials in water to produce a hydrolyzate, which is purified by ion exchange and further hydrolyzed with an enzyme material having proteolytic activity. U.S. Pat. No. 3,842,848 describes aqueous hair treating compositions containing a keratin polypeptide hydrolyzate produced by the acid hydrolysis of hair.

A method for treating hair to improve the manageability, body and sheen thereof is disclosed in U.S. Pat. No. 4,186,188. The method involves the application, from aqueous solution, of certain charged polypeptides formed by the hydrolysis of certain proteins. Mixtures of amino acids and vitamins are disclosed in U.S. Pat. No. 4,201,235 for the purpose of enhancing softness and luster and imparting fuller body to the hair.

U.S. Pat. No. 4,275,748 describes a method of modifying filamentous keratins by contact with an aqueous solution containing, among other ingredients, a collagen polypeptide/amino acid composition.

Compositions for providing improved conditioning of the hair by the application of aqueous compositions containing salts of chitosan are disclosed in U.S. Pat. No. 4,202,881 and French Pat. No. 2,354,760.

While the prior art described above shows that both chitosan and a wide variety of protein hydrolyzate materials have been used in the treatment of human hair in the past, none of the references discloses or suggests the employment of the adducts discovered by us as described hereinafter.

SUMMARY OF THE INVENTION

We have discovered that improved body and set holding capabilities along with improved sheen and combing properties can be imparted to hair by treatment with aqueous compositions containing adducts of (1) oligomers prepared by the controlled acid hydrolysis of chitosan and (2) mixtures of amino acids containing no more than low levels of di- and tri-peptides and which are obtained by the hydrolysis of keratin materials. In a preferred application of the invention, the compositions take the form of hair conditioning compositions and shampoos containing cleansing surfactants. The proportion of the oligomer to the protein hydrolyzate may range in molar ratio from 3:1 to 1:3, with the overall concentration of the adduct ranging from 1–10% by weight, depending upon the product application involved.

DETAILED DESCRIPTION OF THE INVENTION

Chitosan is a high molecular weight polymer amine made by the alkaline deacetylation of chitin, which is a material naturally present in shrimp shells. While the chitosan which is commercially available often contains impurities of 10–30% by weight, these commercial products, as well as products having a higher content of chitosan, can be used equally well for the purposes of our invention.

For use in the practice of our invention, the chitosan is first subjected to hydrolysis in the manner described by Horowitz (Horowitz, S. T. et al., "The Preparation of Glucosamine oligosaccharides. I. Separation", J.A.C.S. 1957, 79, 5046). As a result of this hydrolysis, there is produced a mixture of glucosamine oligomers having the following structure:

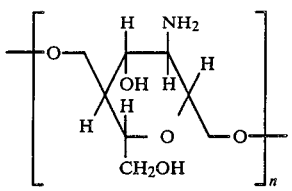

where n is an integer having the value of 1–10. To minimize the formation of adduct on the hair fiber surfaces when applied in admixture with the hydrolyzed keratin protein, it is important that the oligomer mixture should consist primarily of monomer, dimer, and trimer with only low levels of the higher oligomers. To be useful in the practice of our invention, the percentage by weight of the oligomer mixture in which n is 1, 2, or 3 must be at least 70%, while at the same time, the percentage by weight in which n is greater than 6 must be less than 25%.

The protein hydrolyzate, with which the oligomer mixture is combined to form the adduct used in the practice of our invention, is made by hydrolyzing the protein chains of keratin raw materials such as human hair, animal hair, horn, or feathers utilizing a controlled acid hydrolysis process. To achieve water solubility, it is necessary to break down the protein chains to form a mixture consisting primarily of the individual amino acids and in which no more than 5% by weight comprises di- and/or tri-peptides. We prefer to use a product obtained by the hydrolysis of hair keratin having a weight average molecular weight of around 150 and which is obtainable from Croda Inc. under the trademark Crotein HKP. This material is represented as having the following amino acid content:

| AMINO ACID | % W/W |
|---|---|
| Isoleucine | 2.4 |
| Leucine | 4.6 |
| Lysine | 3.6 |
| Methionine | 0.8 |
| Cystine | 1.3 |
| Phenylalanine | 2.3 |
| Threonine | 9.0 |
| Tyrosine | 0.8 |
| Valine | 5.2 |
| Arginine | 9.1 |
| Histidine | 1.3 |
| Alanine | 4.6 |
| Aspartic Acid | 9.0 |
| Glutamic Acid | 18.1 |
| Glycine | 5.6 |
| Proline | 9.3 |
| Serine | 13.1 |

It is possible, however, in the practice of our invention to use other keratin-derived protein hydrolyzates having approximately the same amino acid content and having a weight average molecular weight ranging from 80 to 250.

In preparing the adduct for use in the practice of our invention, the oligomer mixture and hydrolyzed protein mixture are weighed out and then dissolved in distilled water to yield a solution usually having a pH of around 4.5. To maximize the beneficial effects of the adduct on hair fibers, we have found that the pH should be adjusted to about 2.5 by the addition of a suitable acid such as concentrated citric acid. Any undissolved material present at this point is removed by filtration.

In instances where solutions are prepared containing surfactant ingredients, as will be hereinafter discussed in greater detail, the appropriate surfactant is predissolved in the distilled water after which the oligomer mixture and hydrolyzed protein mixture are added and the pH adjusted as described above.

Simple aqueous solutions of the adduct in which the proportion of the oligomer to the protein hydrolzyate may range in molar ratio from 3:1 to 1:3, and in which the overall concentration of the adduct may range from 1–10% by weight, may be applied to the hair in the practice of our invention. It is preferable, however, to include conventional surface active agents either as formulation aids or as primary cleansing ingredients in shampoo-type applications. In either case, it is important that the surfactant be selected to avoid incompatibilities.

In general, any of the usual non-ionic surfactants or mixtures thereof known to those skilled in the art of formulation of products for treating the hair may be employed in formulating the compositions of our invention. Among such non-ionic surface active agents are the ethylene oxide ethers of alkyl phenols such as nonylphenol polyoxyethylene ether, the ethylene oxide ethers of fatty alcohols such as tridecyl alcohol polyoxyethylene ether, the ethylene oxide ethers of alkyl mercaptans such as dodecyl mercaptan polyoxyethylene thioether, the ethylene oxide esters of the fatty acids such as lauric ester of polyethylene glycol and lauric ester of methoxy polyethylene glycol, the ethylene oxide ethers of fatty acid amides, the condensation products of ethylene oxide with partial fatty acid esters of sorbitol such as the lauric ester of sorbitan polyethylene glycol ether, and other similar materials. We especially prefer the non-ionic surfactant sold under the Triton X-100 trademark (Rohm & Haas Co.) having the following structure:

$$C_8H_{17}\text{—}\underset{}{\bigcirc}\text{—}(OCH_2CH_2)_{9-10}OH$$

and the non-ionic surfactant sold under the trademark Tween 20 (ICI Americas Inc.) having the following structure:

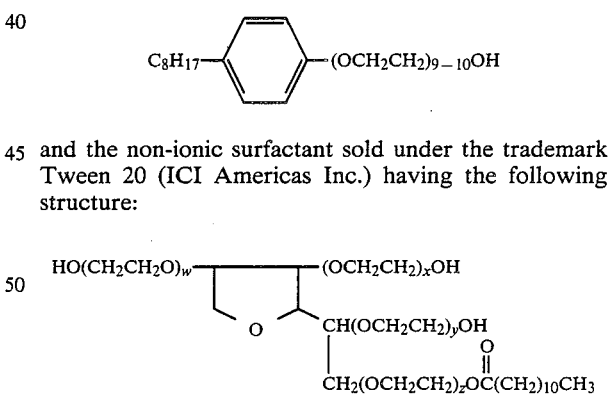

where $w+x+y+z=20$

In the formulation of rinse-type compositions, we usually use about 2% by weight of surface active agent to enhance the application of the composition to the hair. Where it is desired to have a shampoo-type product in which the hair is both cleansed and left with conditioning and setting benefits, we prefer to use from 3–5% by weight of an appropriate surface active agent, as described above. Broadly speaking, as little as 1% or as much as 20% by weight surface active agent may be used without seriously impeding the action of the adduct in providing conditioning, combing, and set holding benefits to the hair.

It will be understood, of course, that various other adjuvents conventionally used in the formulation of hair care products including perfumes, dyes, opacifiers, conditioning agents and the like may likewise be employed in the practice of our invention as long as care is taken to avoid chemical incompatability.

EXAMPLE I-HYDROLYSIS OF CHITOSAN

Into a one liter round bottom flask fitted with a magnetic stirrer and immersed in an oil bath is charged 250 ml of 12N hydrochloric acid. With stirring, 25 grams of Kytex M chitosan (Hercules, Inc.) is added in increments. As the Kytex dissolves, the solution becomes viscous and 250 ml additional acid is charged into the reactor. Once the addition is complete, the temperature of the oil bath is raised to 45° to 50° C. The flask is capped with a stopper fitted with a polytetrafluoroethylene sleeve and the stirred reaction mixture maintained at a bath temperature of 45° to 50° for 48 hours.

At the end of the reaction period, the resulting dark brown solution is reduced in vacuo on a rotary evaporator to a thick syrup (approximately 100 ml final volume). During evaporation, the flask is heated in an oil bath maintained at no more than 40° to 45° C. to prevent additional degradation of the product.

The product is then transferred to a four liter beaker with acetone and additional acetone added to a volume of 3.5 l. The mixture is stirred for one hour, solids allowed to settle and the supernatant decanted. The solid is filtered, then returned to the beaker. Approximately 25 ml distilled water is added and the product precipitated in 3.5 l of acetone. The mixture is stirred for one hour and the solid filtered. Finally, the solid is dispersed in 3.5 l of acetone and again stirred for one hour and filtered. If the product has a tendency to gum out, an additional one or two acetone washes can be performed without great detriment to product yield. Finally the product, a beige powder, is vacuum oven dried for four hours at 40° C. The product is stored in a tightly closed container in a freezer to prevent further degradation. A yield on the order of 80 percent is obtained of a mixture of glucosamine oligomers in which about 80% by weight of the oligomers comprise monomer, dimer, and trimer and in which less than 20% by weight comprises oligomers of greater than six glucosamine units. By varying the normality of the acid used in the hydrolysis and the time the reaction is permitted to continue, the distribution of the oligomer mixture can be controlled. In general, use of lower acid concentrations and/or shorter reaction times will result in oligomer mixtures having a lesser proportion of monomer, dimer, and trimer.

EXAMPLE II-HAIR SETTING AND CONDITIONING COMPOSITION

To 100 ml of distilled water there is added and dissolved 2.36 grams of the chitosan hydrolysis product described in Example I (having an assumed formula weight of 216 for the glucosamine.HCl monomer unit) along with 3.28 grams of an amino acid mixture obtained from the hydrolysis of hair and sold under the trademark Crotein HKP (Croda Inc.). The pH of the resulting solution, which is about 4.5, is adjusted to 2.5 by the addition of concentrated aqueous citric acid. Any insoluble by-product material remaining undissolved is removed at this point by filtration.

The resulting composition is presumed to contain an adduct of the chitosan hydrolysis product and amino acid mixture and may be applied to hair in the same manner as conventional hair setting and conditioning compositions.

EXAMPLE III-CONDITIONING SHAMPOO COMPOSITION

To 81 grams of distilled water there is added and dissolved 15 grams of a polyoxyethylene (2) sorbitan monolaurate sold under the trademark Tween 20 (ICI Americas Inc.). To the resulting solution is added and dissolved 2.36 grams of the chitosan hydrolysis product described in Example I along with 3.28 grams of a protein mixture obtained from the hydrolysis of hair and sold under the trademark Crotein HKP (Croda Inc.). After adjustment of the pH to 2.5 by the addition of concentrated aqueous citric acid, the composition is ready for use as described below.

The conditioning shampoo formulation is evaluated by use by subjects who are treated six times each, half head, with the test composition, employing a commercially available conditioning shampoo as a control. Evaluation of cosmetic attributes shows parity between the two compositions for set holding, fullness, sheen and cleansing, with the test composition outperforming the control composition in combing, manageability, softness, lack of coated feel, and, to some extent, control of fly-away.

Having thus disclosed the invention, what is claimed is:

1. A hair-treating composition selected from the class consisting of hair setting, shampoo, and conditioning compositions comprising an aqueous solution containing from about 1 to about 10% by weight of an adduct of an oligomer of hydrolyzed chitosan and a mixture of amino acids obtained from the hydrolysis of a keratin raw material selected from the class consisting of human hair, animal hair, horn, and feathers and which has a weight average molecular weight of about 80 to 250 has been inserted in claim 9, line 9, said hydrolyzed chitosan being a mixture of glucosamine oligomers having the following structure:

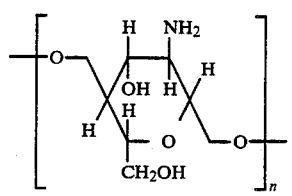

where n is an integer having the value of 1-10, the percentage by weight of the oligomer mixture in which n is 1, 2, or 3 is at least 70% and in which the percentage by weight of the oligomer in which n is greater than 6 is less than 25%, the proportion of hydrolyzed chitosan to amino acid mixture being from 3:1 to 1:3.

2. A hair-treating composition as described in claim 1 having a pH of about 2.5.

3. A hair-treating composition as described in claim 1 containing, in addition, from 2 to 20% by weight of a nonionic surface active agent.

4. A method for providing set holding and conditioning benefits to hair comprising the application of the composition described in claim 1.

* * * * *

UNITED STATES PATENT AND TRADEMARK OFFICE
CERTIFICATE OF CORRECTION

PATENT NO. : 4,542,014

DATED : September 17, 1985

INVENTOR(S) : Ann F. Bresak and Eva Tolgyesi

It is certified that error appears in the above-identified patent and that said Letters Patent is hereby corrected as shown below:

Column 6, line 41 - delete "has been inserted in claim 9, line 9"

and insert

-- and contains no more than 5% by weight di and/or tri-peptides --

Signed and Sealed this

First Day of July 1986

[SEAL]

Attest:

DONALD J. QUIGG

Attesting Officer

Commissioner of Patents and Trademarks